(12) United States Patent
Silvestrini et al.

(10) Patent No.: US 10,531,695 B2
(45) Date of Patent: Jan. 14, 2020

(54) CARTRIDGE FOR AN AEROSOL-GENERATING SYSTEM

(71) Applicant: Altria Client Services LLC, Richmond, VA (US)

(72) Inventors: Patrick Charles Silvestrini, Neuchatel (CH); Ihar Nikolaevich Zinovik, Peseux (CH)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 16/436,064

(22) Filed: Jun. 10, 2019

(65) Prior Publication Data
US 2019/0289917 A1 Sep. 26, 2019

Related U.S. Application Data

(63) Continuation of application No. 15/609,303, filed on May 31, 2017, now Pat. No. 10,342,262, which is a
(Continued)

(30) Foreign Application Priority Data

May 31, 2016 (EP) .................................... 16172074

(51) Int. Cl.
*A24F 47/00* (2006.01)
*B23K 1/00* (2006.01)
*H05B 1/02* (2006.01)

(52) U.S. Cl.
CPC .......... *A24F 47/008* (2013.01); *B23K 1/0016* (2013.01); *H05B 1/0227* (2013.01); *H05B 2203/021* (2013.01)

(58) Field of Classification Search
CPC ..................................................... A24F 47/008
See application file for complete search history.

(56) References Cited

U.S. PATENT DOCUMENTS

| 5,498,855 A | 3/1996 | Deevi et al. |
| 5,530,225 A | 6/1996 | Hajaligol |

(Continued)

FOREIGN PATENT DOCUMENTS

| EP | 0703735 A1 | 4/1996 |
| GB | 2504076 A | 1/2014 |

(Continued)

OTHER PUBLICATIONS

Extended European Search Report Application No. 16172074.3-1662 dated Dec. 5, 2016.
(Continued)

*Primary Examiner* — James Harvey
(74) *Attorney, Agent, or Firm* — Harness, Dickey & Pierce, P.L.C.

(57) ABSTRACT

A cartridge for an aerosol-generating system may comprise a liquid storage portion, which includes a housing holding a liquid aerosol-forming substrate. The housing has a first and a second opening. The cartridge may further comprise a first and a second permeable planar heater assembly, wherein the first permeable planar heater assembly is fixed to the housing and extends across the first opening of the housing, and the second permeable planar heater assembly is fixed to the housing and extends across the second opening of the housing. The first and second permeable planar heater assemblies are arranged opposite each other such that they face each other and form an airflow channel in between.

20 Claims, 4 Drawing Sheets

Related U.S. Application Data continuation of application No. PCT/EP2017/060393, filed on May 2, 2017.

(56) References Cited

U.S. PATENT DOCUMENTS

| | | | |
|---|---|---|---|
| 10,045,567 B2* | 8/2018 | Monsees | A24F 47/008 |
| 2014/0270730 A1 | 9/2014 | DePiano et al. | |
| 2014/0305449 A1 | 10/2014 | Plojoux et al. | |
| 2015/0027470 A1 | 1/2015 | Kane et al. | |
| 2016/0338410 A1* | 11/2016 | Batista | A24F 47/008 |
| 2016/0345629 A1 | 12/2016 | Mironov | |
| 2017/0095624 A1* | 4/2017 | Davidson | A61M 15/005 |
| 2017/0105452 A1 | 4/2017 | Mironov et al. | |
| 2017/0340013 A1 | 11/2017 | Silvestrini et al. | |
| 2017/0354184 A1 | 12/2017 | Mironov et al. | |
| 2018/0014575 A1* | 1/2018 | Fursa | A24F 47/008 |
| 2018/0020737 A1* | 1/2018 | Mironov | F16T 1/00 131/329 |
| 2018/0184713 A1 | 7/2018 | Mironov et al. | |
| 2018/0242642 A1* | 8/2018 | Silvesstrini | A24F 47/008 |
| 2018/0310622 A1 | 11/2018 | Mironov et al. | |
| 2019/0000148 A1 | 1/2019 | Atkins et al. | |

FOREIGN PATENT DOCUMENTS

| | | |
|---|---|---|
| WO | WO-2013/152873 A1 | 10/2013 |
| WO | WO-2014/071329 A1 | 5/2014 |
| WO | WO-2015/117702 A1 | 8/2015 |
| WO | WO-2015/117704 A1 | 8/2015 |
| WO | WO-2015177046 A1 | 11/2015 |
| WO | WO-2016/005600 A1 | 1/2016 |

OTHER PUBLICATIONS

Written Opinion for Application No. PCT/EP2017/060393 dated Jul. 28, 2017.
International Search Report and Written Opinion for Application No. PCT/EP2017/060393 dated Jul. 31, 2017.
International Preliminary Report on Patentability and Written Opinion for Application No. PCT/EP2017/060393 dated Dec. 13, 2018.

* cited by examiner

CARTRIDGE FOR AN AEROSOL-GENERATING SYSTEM

CROSS-REFERENCE TO RELATED APPLICATIONS

This is a continuation under 35 U.S.C. § 120 of U.S. application Ser. No. 15/609,303, filed on May 31, 2017, which is a continuation of and claims priority to PCT/EP2017/060393, filed on May 2, 2017, and further claims priority to EP 16172074.3, filed on May 31, 2016, each of which are hereby incorporated by reference in their entirety.

BACKGROUND

Field

The present disclosure relates to a cartridge for an aerosol-generating system, such as a handheld electrically-operated system, and an aerosol-generating system comprising the cartridge.

Description of Related Art

Handheld electrically-operated aerosol-generating systems are known that consist of a main body comprising a battery and electric circuitry and a cartridge comprising a supply of aerosol-forming substrate held in a liquid storage portion. In aerosol-generating systems, a heater assembly is disclosed to vaporise the liquid aerosol-forming substrate, wherein the heater assembly has the form of a flat mesh extending across an opening of the liquid storage portion. The flat mesh may be provided at a side surface of the liquid storage portion such that an airflow channel is created adjacent to the liquid storage portion with the flat mesh on one side of the airflow channel and the housing of the cartridge on the other side of the airflow channel. The air flowing through this channel is exposed to a hot side, where the flat mesh is arranged, and a cooler side, where the housing is arranged. Due to the relatively large temperature difference between the two sides, an unwanted condensation of aerosol droplets may occur at the cartridge housing.

SUMMARY

According to some example embodiments, there is provided a cartridge for an aerosol-generating system. The cartridge comprises a liquid storage portion, which comprises a housing holding a liquid aerosol-forming substrate. The housing has a first and a second opening. The cartridge further comprises a first and a second heater assembly (e.g., permeable planar heater assembly), wherein the first heater assembly is fixed to the housing and extends across the first opening of the housing, and the second heater assembly is fixed to the housing and extends across the second opening of the housing. The first and second permeable heater assemblies are arranged opposite each other such that they face each other and form an airflow channel in between each other.

The first and second heater assemblies may be substantially flat or planar. As used herein, "substantially flat" means formed in a single plane and not wrapped around or other conformed to fit a curved or other non-planar shape. A flat heater assembly can be handled with relative ease during manufacture and provides for a robust construction. A "substantially flat" heater assembly means an heater assembly that is in the form of a substantially two dimensional object. Thus, a substantially flat heater assembly extends in two dimensions substantially more than in a third dimension. In particular, the dimensions of the substantially flat heater assembly in each of the two dimensions is at least 5 times larger than in the third dimension.

Providing at least two heater assemblies which are facing each other allows air, flowing through the airflow channel, to not be in contact with a hot side and a cold side, but to be heated relatively uniformly from two sides. Consequently, a more uniform aerosol will form in the airflow channel, since the air is not cooled on one side. Otherwise, an aerosol may be formed adjacent to the heater assembly and cooled at the opposite side of the heater assembly near the cartridge wall. At this cold side of the cartridge, undesired droplets may form on the cartridge wall, thereby decreasing the quality of the generated aerosol. Furthermore, the quality of the generated aerosol may depend on the outside temperature, which in turn determines the temperature of the wall of the cartridge. The example embodiments herein may overcome these disadvantages by providing a further heater assembly opposite the first heater assembly. The forming of an aerosol by vaporisation of the liquid aerosol-forming substrate from the liquid storage portion is therefore no longer deteriorated by the relatively cool side wall of the cartridge. Instead, by providing two heater assemblies facing each other, the droplet size of the generated aerosol as well as the temperature, to which the on-rushing air is heated, may be adjusted independent of the outside circumstances, i.e. independent of outside parameters.

The airflow channel is provided in the cartridge such that the first heater assembly is provided on one side of the airflow channel and the other heater assembly is provided on the other side of the airflow channel. Also, more than two heater assemblies may be provided. If more than two heater assemblies are provided, these heater assemblies are then fixed to the housing of the liquid storage portion and extend across respective openings of the housing. If more than two heater assemblies are provided, these heater assemblies may be arranged to form a triangle (e.g., for three heater assemblies), wherein the airflow channel is provided in the middle of the triangle between the heater assemblies. More than three heater assemblies may be arranged to define an airflow channel between the heater assemblies.

The first heater assembly may electrically be connected to the second heater assembly by an electrical bridging connection (e.g., a soldered connection). Thus, only one electrical connection is necessary between a power supply and the heater assemblies. In an example embodiment, the first heater assembly comprises a first contact region and the second heater assembly comprises a second contact region to enable the flow of an electric current through the first and second heater assembly. If the heater assemblies are not electrically connected to each other, each heater assembly comprises two contact portions and two electrical connections are provided between the respective contact portions of the heater assemblies and a power supply.

The electrical connection may be provided integrally with the housing of the liquid storage portion. Thus, the costs of the cartridge may be reduced due to the cartridge comprising fewer components.

The soldered connection may be provided on a side surface of the first or second heater assembly directly adjacent to the liquid aerosol-forming substrate. By providing the soldered connection directly adjacent to the liquid aerosol-forming substrate, the soldered connection may aid the heating process. In more detail, providing the soldered connection near to the liquid aerosol-forming substrate may lead to the effect that the flow of electric current through the soldered connection heats the soldered connection, thereby heating the adjacent liquid aerosol-forming substrate.

Heating the adjacent liquid aerosol-forming substrate may enhance the performance of the assembly. This may reduce the viscosity of the liquid which may increase the flow of the liquid to the heater assembly, thereby increasing the surface of the heater assembly that is covered or submerged in the liquid and minimizing the risk of overheating. When the aerosol-generating system is not in use, the viscosity of the unheated liquid may reduce the occurrence of undesirable leakage to and through the heater assembly.

The heater assemblies may not extend along the full length of the cartridge. For instance, the heater assemblies may extend along 5 percent to 60 percent of the length of the cartridge. In another instance, the heater assemblies may extend along 10 percent to 40 percent of the length of the cartridge (e.g., about 20 percent of the full length of the cartridge).

The cartridge thus comprises a first portion in which the heater assemblies are provided and in which liquid aerosol-forming substrate is vaporised by the heater assemblies, thereby generating an aerosol, and a second portion in which the generated aerosol can cool. The length of the first portion may be between 1 millimeter and 10 millimeters. For instance, the length of the first portion may be between 3 millimeters and 7 millimeters (e.g., around 5 millimeters). The length of the second portion may be chosen such that aerosol-droplets of a desired size may form due to the cooling of the aerosol in the second portion. The length of the second portion may be between 1 centimeter and 5 centimeters. For instance, the length of the second portion may be between 2 centimeters and 4 centimeters (e.g., around 3 centimeters). Consequently, the first portion may have a length of between 10 percent to 30 percent of the length of the cartridge or the second portion. For instance, the first portion may have a length of between 15 percent to 25 percent (e.g., about 20 percent) of the length of the cartridge or the second portion. Thus, a homogeneous aerosol of relatively consistent high quality may be generated in the airflow channel and the droplet size of the generated aerosol may be adjusted by the length of the subsequent second portion of the cartridge. Thus, a desired droplet size may be generated. The droplet size may be smaller than 3 microns. For instance, the droplet size may be smaller than 2 microns. In another instance, the droplet size may be smaller than 1 micron (e.g., about 0.4 microns).

In some example embodiments, the heater assemblies are spaced apart from each other by 0.25 millimeters to 2 millimeters. For instance, the heater assemblies may be spaced apart from each other by 0.75 millimeters to 1.25 millimeters (e.g., 1 millimeter).

The distance between the heater assemblies defines the diameter of the airflow channel. The above distances lead to the effect that a relatively homogeneous aerosol is generated by the heater assemblies, while a sufficient amount of air per time can pass through the airflow channel.

The heater assemblies may comprise mesh heaters. The mesh heaters may be substantially flat or planar. In more detail, the heater assemblies may each comprise a plurality of electrically conductive filaments connected to first and second electrically conductive contact portions, the first and second electrically conductive contact portions may be positioned on opposite sides of the respective heater assembly. The first and second electrically conductive contact portions are configured to allow contact with an external power supply. The plurality of electrically conductive filaments may form a mesh or array of filaments or may comprise a woven or non-woven fabric.

The electrically conductive filaments may form a mesh of size between 160 and 600 Mesh US (+/−10 percent) (e.g., between 400 and 1500 filaments per centimeter (+/−10 percent)). The width of interstices may be between 75 microns and 25 microns. The percentage of open area of the mesh, which is the ratio of the area of the interstices to the total area of the mesh may be between 25 and 56 percent. The mesh may be formed using different types of weave or lattice structures. Alternatively, the electrically conductive filaments may consist of an array of filaments arranged parallel to one another.

The mesh, array, or fabric of electrically conductive filaments may also be characterised by its ability to retain liquid, as is well understood in the art.

The electrically conductive filaments may have a diameter of between 8 microns and 100 microns. For instance, the diameter may be between 8 microns and 50 microns (e.g., between 8 microns and 39 microns).

The area of the mesh, array, or fabric of the electrically conductive filaments may be relatively small (e.g., less than or equal to 25 square millimetres), allowing it to be incorporated into a handheld system. The mesh, array, or fabric of electrically conductive filaments may, for example, be rectangular and have dimensions of 6 square millimeters by 6 square millimetres. For instance, the dimensions may be 5 square millimeters by 5 square millimetres. In another instance, the dimensions may be 4 square millimeters by 4 square millimetres. In another instance, the dimensions may be 3 square millimeters by 3 square millimetres. In another instance, the dimensions may be 2 square millimeters by 2 square millimetres. Furthermore, combinations of the above dimensions are possible.

The electrical resistance of the mesh, array, or fabric of electrically conductive filaments of the heater assembly may be between 0.3 and 4 Ohms. For example, the electrical resistance of the mesh, array, or fabric of electrically conductive filaments may be between 0.5 and 3 Ohms (e.g., about 1 Ohm). The electrical resistance of the mesh, array, or fabric of electrically conductive filaments may be at least an order of magnitude (e.g., at least two orders of magnitude) greater than the electrical resistance of the contact portions. This ensures that the heat generated by passing current through the heater assembly is localised at the mesh or array of electrically conductive filaments. It is beneficial to have a relatively low overall resistance for the heater element if the system is powered by a battery. Reducing or minimizing parasitic losses between the electrical contacts and the mesh or the filaments may also be desirable to reduce or minimize parasitic power losses. A relatively low resistance, high current system allows for the delivery of relatively high power to the heater element. This allows the heater element to heat the electrically conductive filaments to a desired temperature more quickly.

The cartridge may comprise a mouthpiece. Alternatively, the cartridge may only be comprised of the liquid storage portion, the housing of the liquid storage portion, and the heater assemblies.

The liquid storage portion is arranged on the inside of the cartridge such that the housing of the liquid storage portion may safely store the liquid aerosol-forming substrate. The housing of the liquid storage portion may be a part of the housing of the cartridge. The heater assemblies are provided on openings of the liquid storage portion. A capillary material having a spongy or fibrous structure may be provided between the heater assemblies and the liquid storage portion such that the liquid aerosol-forming substrate may be conveyed from the inside of the liquid storage portion to the heater assemblies without leaking from the liquid storage portion. As a result, the heater assemblies may be moistened with liquid aerosol-forming substrate in this manner.

According to some example embodiments, the cartridge comprises two separate liquid storage portions. The first liquid storage portion may comprise a first housing with a first opening with the first heater assembly extending across the first opening of the first housing, and the second liquid storage portion may comprise a second housing with a second opening with the second heater assembly extending across the second opening of the housing. The first and second permeable heater assemblies are arranged opposite each other such that they face each other and form an airflow channel in between each other. All features described in connection with example embodiments discussed above also apply to this example embodiment.

By providing two separate liquid storage portions, two different liquid aerosol-forming substrates may be provided in the two liquid storage portions. Also, the separate liquid storage portions may be arranged with relative ease in the cartridge opposite each other such that the first and second heater assembly face each other and form an airflow channel in between each other.

The first or second or both housing(s) may hold any suitable liquid aerosol-forming substrate. The liquid aerosol-forming substrate may comprise glycerol, pyruvic acid, lactic acid, glycerine, or any combination thereof. The aerosol-forming substrate may comprise other additives and ingredients, such as flavourings or tobacco or nicotine or combinations thereof. In an example embodiment, the first housing contains a liquid aerosol-forming substrate with nicotine or tobacco but without flavourings, and the second housing contains a liquid aerosol-forming substrate with flavourings but without nicotine or tobacco.

The first and the second housing may thus be utilized to hold different liquid aerosol-forming substrates. This may be used to separate ingredients such as nicotine or nicotine flavour from other substrates such as glycerol, pyruvic acid, and/or lactic acid (e.g., glycerol and pyruvic acid, glycerol and lactic acid, pyruvic acid and lactic acid, or glycerol and pyruvic acid and lactic acid).

The first and second housing may be symmetrical half-cylinders and the airflow channel in between the heater assemblies may be a central airflow channel.

Thus, a symmetric airflow channel is provided which facilitates that a homogeneous aerosol is generated during vaporisation of the liquid aerosol-forming substrates by the heater assemblies.

According to some example embodiments, an aerosol-generating system is provided. The aerosol-generating system comprises a main body with a power supply, electric circuitry, and a cartridge. The cartridge may be as described in connection with example embodiments discussed above. The cartridge is coupled (e.g., replaceably coupled) to the main body. The main body further comprises an air inlet such that air can be drawn through the air inlet and the airflow channel of the cartridge to a mouthpiece.

In a non-limiting embodiment, the air is ambient air and is drawn from the outside of the aerosol-generating system. When the air is drawn through the airflow channel, the aerosol-generating system may be manually activated or automatically activated by a sensor such that the heater assemblies are heated. In order to heat the heater assemblies, the electric circuitry may control a flow of electric current from the power supply through the heater assemblies. Then, liquid aerosol-forming substrate from the liquid storage portion is vaporised by the heater assemblies, thereby creating an aerosol in the airflow channel. The aerosol subsequently exits through the mouthpiece.

The electric circuitry may be electrically connected to the power supply. The electric circuitry may be configured to monitor the electrical resistance of the heater assemblies, when the cartridge is coupled to the main unit. The electric circuitry may be configured to control a supply of electric current from the power supply to the heater assemblies depending on the electrical resistance of the heater assemblies.

The electric circuitry may optimize the control of the heater assemblies by measuring the electrical resistance of the heater assemblies and controlling the supply of electric current from the power supply to the heater assemblies depending on the electrical resistance of the heater assemblies. In an example embodiment, the material of the heater assemblies is an electrically conductive material satisfying the equation $$R(t) = R(t_0)(1 + \alpha_{t_0}(t - t_0))$$

wherein $\alpha$ is the temperature coefficient of resistance, $t_0$ is a fixed reference temperature (e.g., room temperature), and $R(t_0)$ is the resistance at temperature $t_0$. If the material of the heater assemblies is known and the electrical resistance is measured, the temperature $t$ of the heater assemblies can be determined. The temperature of the heater assemblies may thus be controlled such that a homogeneous aerosol of relatively consistent quality may be produced by the heater assemblies in the airflow channel. Furthermore, a burning of the contents of the liquid storage portion(s) may be prevented. This may also prevent or reduce the thermal decomposition of the liquid.

A process for manufacturing a cartridge for an aerosol-generating system may comprise providing a liquid storage portion, comprising a housing holding a liquid aerosol-forming substrate, the housing having a first and a second opening, fixing a first permeable heater assembly to the housing so that the first permeable heater assembly extends across the first opening of the housing, fixing a second permeable heater assembly to the housing so that the second permeable heater assembly extends across the second opening of the housing, and arranging the first and second permeable heater assemblies opposite each other such that they face each other and form an airflow channel in between each other.

A process for manufacturing a cartridge for an aerosol-generating system may also comprise providing a first liquid storage portion, comprising a first housing holding a liquid aerosol-forming substrate, the housing having a first opening, fixing a first permeable heater assembly to the first housing so that the first permeable heater assembly extends across the first opening of the first housing, providing a second liquid storage portion, comprising a second housing, the second housing having a second opening, fixing a second permeable heater assembly to the second housing so that the second permeable heater assembly extends across the second opening of the second housing, and arranging the first and second permeable heater assemblies opposite each other such that they face each other and form an airflow channel in between each other.

In some example embodiments, the process may comprise the further step of connecting the heater assemblies electrically by a bridging connection. Thus, the heater assemblies may be connected to a power supply with a single connection, thereby reducing the number of components required.

The bridging connection may be provided by soldering the first permeable heater assembly to the second permeable heater assembly.

It should be understood that the features described in relation to one example embodiment may equally be applied to other relevant example embodiments of the disclosure although not explicitly set forth herein.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
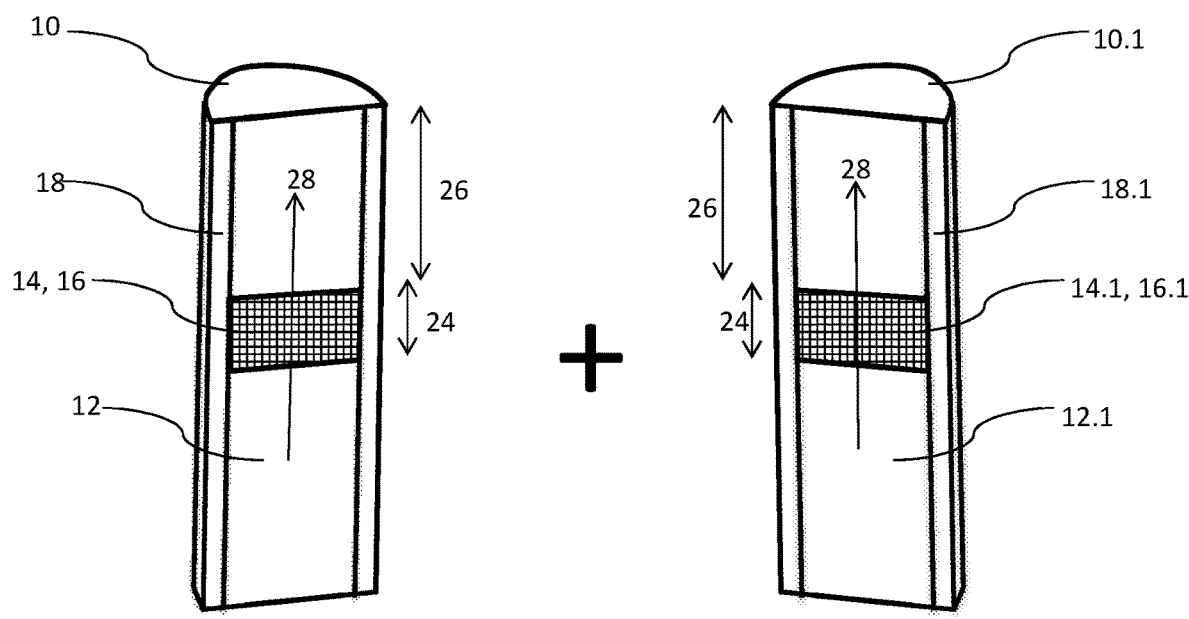
FIG. 1 is a sectional view of an example embodiment of a cartridge.
Figure 2:
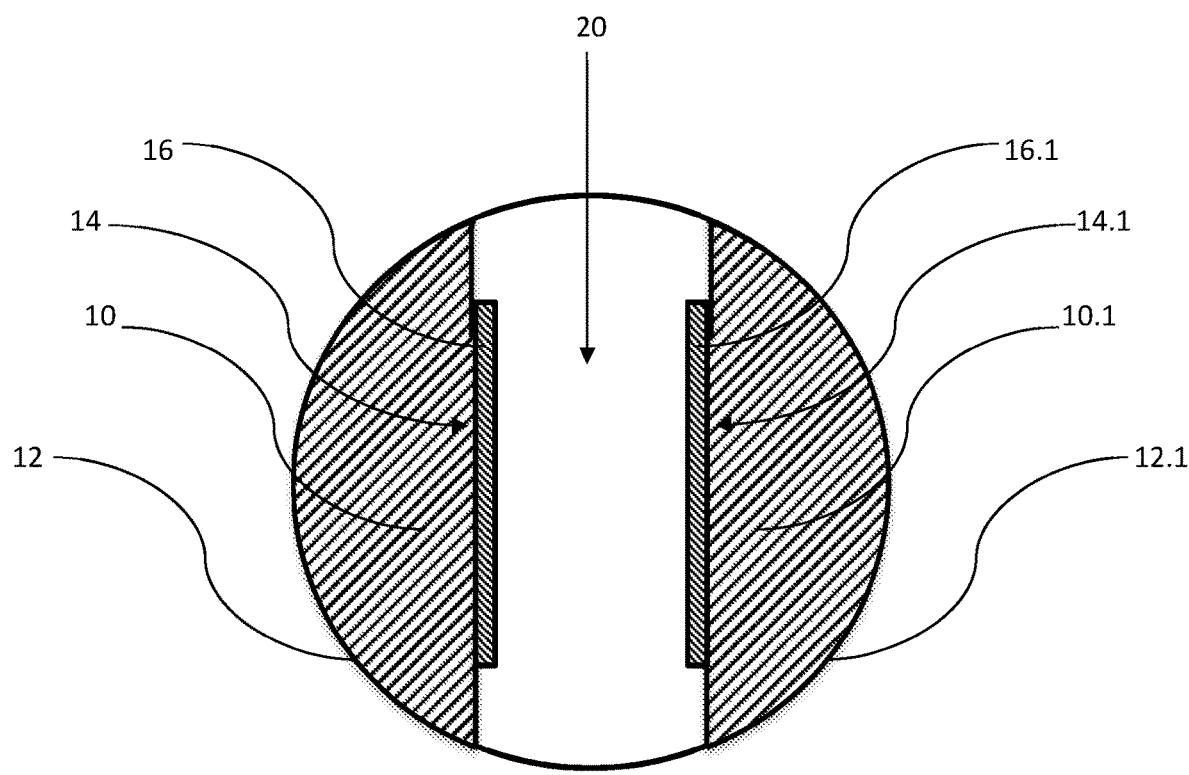
FIG. 2 is a further sectional view of an example embodiment of a cartridge.
Figure 3:
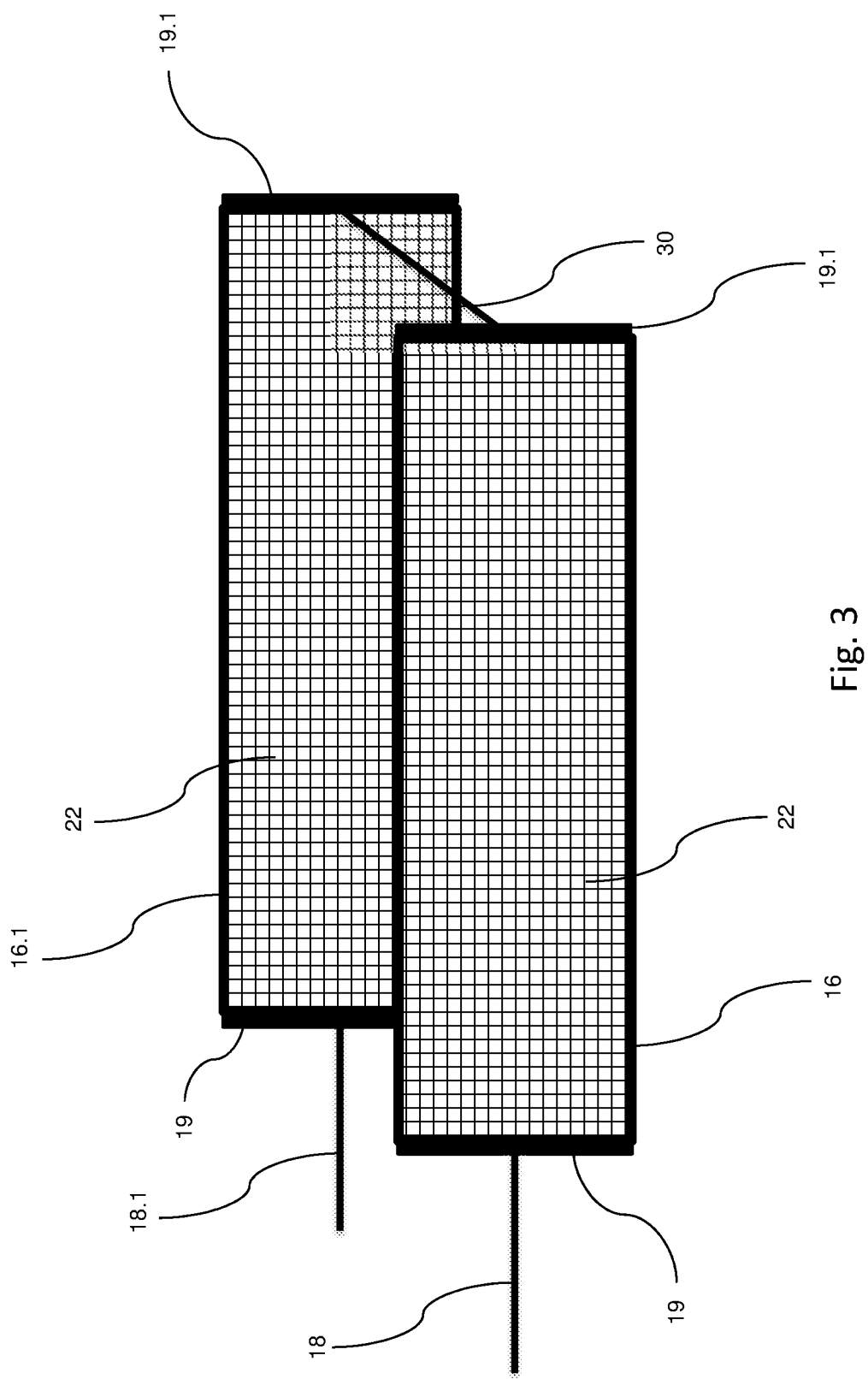
FIG. 3 is an illustrative view of an example embodiment of a first and second heater assembly.
Figure 4:
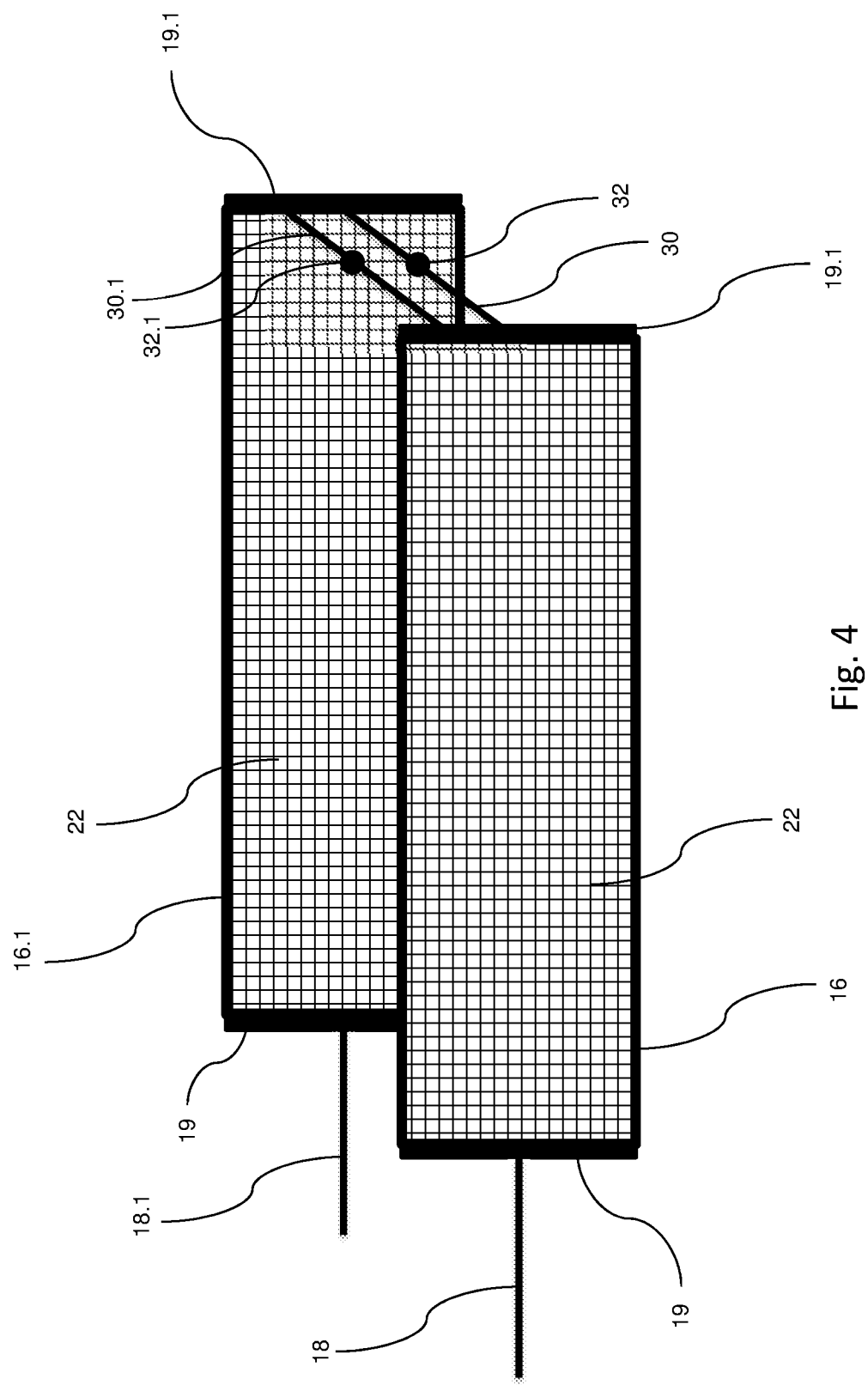
FIG. 4 is an illustrative view of another example embodiment of a first and second heater assembly.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 shows an example embodiment of a cartridge. The cartridge comprises a first liquid storage portion 10. The cartridge may also include a second liquid storage portion 10.1. The first liquid storage portion 10 and the second liquid storage portion 10.1 are provided separate from each other such that each liquid storage portion separately encloses a liquid aerosol-forming substrate. The first liquid storage portion 10 may hold an aerosol-forming substrate comprising 40% by weight glycerine, 40% by weight propylene glycol, 20% by weight water, and flavourings. The second liquid storage portion 10.1 may hold an aerosol-forming substrate comprising nicotine and no flavourings.

The first liquid storage portion 10 comprises a first housing 12 and the second liquid storage portion 10.1 comprises a second housing 12.1. The first housing 12 comprises a first opening 14 and the first second 12.1 comprises a second opening 14.1. Through the openings 14, 14.1, liquid aerosol-forming substrate can flow from the inside of the housings 12, 12.1 to the outside of the housings 12, 12.1. The openings 14, 14.1 are covered with permeable heater assemblies 16, 16.1. In other words, a first permeable heater assembly 16 extends across the first opening 14 and a second permeable heater assembly 16.1 extends across the second opening 14.1.

The permeable heater assemblies 16, 16.1 are provided to heat the liquid aerosol-forming substrate, thereby generating an aerosol. By providing two permeable heater assemblies 16, 16.1, twice the amount of liquid aerosol-forming substrate can be vaporized. Adjacent to the permeable heater assemblies 16, 16.1 inside the housings 12, 12.1, capillary elements (not shown in the Figures) can be provided. The capillary elements can be provided to convey the liquid aerosol-forming substrate from the inside of the housings 12, 12.1 to the permeable heater assemblies 16, 16.1.

In order to heat the permeable heater assemblies 16, 16.1, the permeable heater assemblies 16, 16.1 are provided with contact portions 19, 19.1 such that an electric current can flow through the permeable heater assemblies 16, 16.1, thereby heating the permeable heater assemblies 16, 16.1. Furthermore, the permeable heater assemblies 16, 16.1 may be provided as a mesh wherein the permeable heater assemblies 16, 16.1 each comprise multiple electrically conductive filaments 22. The electrically conductive filaments 22 are provided to enable liquid aerosol-forming substrate to permeate through the permeable heater assemblies 16, 16.1. The surface of the permeable heater assemblies 16, 16.1, which can be utilized for vaporising the liquid aerosol-forming substrate, are thus enlarged. The electrically conductive filaments 22 run parallel to the side surfaces of the permeable heater assemblies 16, 16.1. The electrically conductive filaments 22 may also run diagonal to the side surfaces of the permeable heater assemblies 16, 16.1.

The aerosol is generated adjacent to the permeable heater assemblies 16, 16.1 in an airflow channel 20. The airflow channel 20 is arranged between the permeable heater assemblies 16, 16.1 within the cartridge. The airflow channel 20 may be provided as a central channel within the cartridge.

Due to the airflow channel 20 being arranged between the permeable heater assemblies 16, 16.1, the liquid aerosol-forming substrate is heated and vaporised from two sides. Thus, a relatively homogeneous aerosol is created in the airflow channel. To facilitate a more homogeneous generation of aerosol, more than two permeable heater assemblies 16, 16.1 can be provided. For example, three heater assemblies can be provided to form an airflow channel with a triangular shape.

In FIG. 1, the permeable heater assemblies 16, 16.1 do not extend along the full height of the cartridge. Thus, an aerosol is created by the permeable heater assemblies 16, 16.1 in a first portion 24 of the cartridge and the aerosol can cool while flowing through the rest of the cartridge, i.e. through a second portion 26 of the cartridge in the flow direction 28. While cooling, larger droplets form in the aerosol. The length of the first portion 24 cartridge may be 5 millimeters and the length of the second portion 26 cartridge may be 3 centimeters. The length of the first portion 24 may be around 16 percent of the length of the second portion 26.

The permeable heater assemblies 16, 16.1 are electrically connected to each other by means of an electrical connection 30. Thus, the first permeable heater assembly 16 and the second permeable heater assembly 16.1 may each be connected at the first contact portion 19 to a power supply of an aerosol-generating system. The first contact portion 19 is connected to the power supply by means of electric connectors 18, 18.1.

The electrical connection 30 is provided to preheat the flow of air, flowing through the permeable heater assemblies 16, 16.1 in the flow direction 28. Thus, less air cools on the mesh of the permeable heater assemblies 16, 16.1, which in turn leads to a smaller temperature gradient along the mesh patches. Consequently, more uniform thermal conditions of vaporization and narrower droplet size distribution of the produced aerosol is/are achieved.

Depicted in FIG. 4 are two electrical connections 30, 30.1. Multiple electrical connections may be provided between the permeable heater assemblies 16, 16.1. Thus, the preheating of the flow of air may be improved.

In FIG. 4, the first electrical connection 30 is provided with a first contact 32 and the second electrical connection 30.1 is provided with a second contact 32.1. By the contacts 32, 32.1 and the voltage applied by means of the two contact portions 19, a wheatstone bridge is created. The wheatstone bridge is utilized to measure the electrical resistance of the permeable heater assemblies 16, 16.1. In this regard, the voltage between the first contact 32 and the second contact 32.1 is measured. If a non-zero voltage is measured, a nonuniform resistance of the permeable heater assemblies 16, 16.1 is detected. In other words, if a non-zero voltage is measured, the electrical resistance of the first permeable heater assembly 16 is different from the electrical resistance of the second permeable heater assembly 16.1. Consequently, also a different temperature of the two permeable heater assemblies 16, 16.1 is detected, since a different electrical resistance leads to different temperatures during heating of the permeable heater assemblies 16, 16.1. Thus, by means of the contacts 32, 32.1, the resistance and temperature of the two permeable heater assemblies 16, 16.1 is monitored.

The cartridge is provided connectable to the aerosol-generating system. The cartridge may be provided as a one-use cartridge, which is disposed once the liquid aerosol-forming substrate in the liquid storage portions 10, 10.1 is depleted. Alternatively, the cartridge may be configured for refilling and reuse.

During use, an application of negative pressure on the aerosol-generating system activates the permeable heater assemblies 16, 16.1 such that the permeable heater assemblies 16, 16.1 vaporise the liquid aerosol-forming substrate. A flow sensor may be provided to sense the application of negative pressure on the aerosol-generating system. Upon detection of the application of negative pressure on the aerosol-generating system, the electric circuitry controls a flow of electric current through the permeable heater assemblies 16, 16.1.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. A cartridge for an aerosol-generating system, comprising:

a housing defining a first opening and a second opening, the housing configured to hold an aerosol-forming substrate within and to release the aerosol-forming substrate therefrom via the first opening and the second opening;

a first permeable heater covering the first opening of the housing; and a second permeable heater covering the second opening of the housing, the first permeable heater and the second permeable heater defining an airflow channel in between.

2. The cartridge according to claim 1, wherein the housing is in a form of a first housing and a second housing.

3. The cartridge according to claim 2, wherein the first housing is configured to hold a first composition of the aerosol-forming substrate, and the second housing is configured to hold a second composition of the aerosol-forming substrate.

4. The cartridge according to claim 2, wherein the first housing defines the first opening, and the second housing defines the second opening.

5. The cartridge according to claim 4, wherein the first permeable heater is fixed to the first housing so as to extend across the first opening, and the second permeable heater is fixed to the second housing so as to extend across the second opening.

6. The cartridge according to claim 2, wherein the first housing and the second housing are symmetrical.

7. The cartridge according to claim 2, wherein the first housing is a first half-cylinder, and the second housing is a second half-cylinder.

8. The cartridge according to claim 7, wherein the first permeable heater is on a planar face of the first half-cylinder, and the second permeable heater is on a planar face of the second half-cylinder.

9. The cartridge according to claim 1, wherein the first permeable heater and the second permeable heater are configured to heat the aerosol-forming substrate released from the first opening and the second opening, respectively.

10. The cartridge according to claim 1, wherein the first permeable heater and the second permeable heater each extend along 5 percent to 60 percent of a full length of the cartridge.

11. The cartridge according to claim 10, wherein the first permeable heater and the second permeable heater each extend along 10 percent to 40 percent of the full length of the cartridge.

12. The cartridge according to claim 1, wherein the first permeable heater and the second permeable heater are spaced apart from each other by 0.25 millimeters to 2 millimeters.

13. The cartridge according to claim 12, wherein the first permeable heater and the second permeable heater are spaced apart from each other by 0.75 millimeters to 1.25 millimeters.

14. The cartridge according to claim 1, wherein the first permeable heater and the second permeable heater each include a plurality of electrically conductive filaments.

15. The cartridge according to claim 14, wherein the first permeable heater and the second permeable heater are in a form of a mesh.

16. The cartridge according to claim 1, wherein the airflow channel between the first permeable heater and the second permeable heater is a central airflow channel.

17. The cartridge according to claim 1, wherein the first permeable heater is electrically connected to the second permeable heater by a first electrical connection.

18. The cartridge according to claim 17, wherein the first electrical connection is configured to heat a flow of air in the airflow channel.

19. The cartridge according to claim 17, wherein the first permeable heater is further electrically connected to the second permeable heater by a second electrical connection.

20. The cartridge according to claim 19, wherein the first electrical connection and the second electrical connection are in a form a wheatstone bridge configured to measure an electrical resistance of each of the first permeable heater and the second permeable heater.

* * * * *